United States Patent [19]
Martinez

[11] Patent Number: 6,013,491
[45] Date of Patent: Jan. 11, 2000

[54] FIBROUS CELLULOSE SUPPORT CONTAINING ADHERED YEAST FOR CONVERTING SUCROSE TO GLUCOSE AND FRUCTOSE

[76] Inventor: Leticia Martinez, 10808 Lake Gardens, #B, Dallas, Tex. 75218

[21] Appl. No.: 08/908,147

[22] Filed: Aug. 6, 1997

[51] Int. Cl.[7] .............................. C12P 19/02; C12N 11/02; C12N 11/12
[52] U.S. Cl. ........................... 435/105; 435/177; 435/179
[58] Field of Search ..................................... 435/105, 174, 435/177, 179

[56] References Cited

U.S. PATENT DOCUMENTS

| | | | |
|---|---|---|---|
| 3,708,397 | 1/1973 | Sipos | 195/31 |
| 3,796,634 | 3/1974 | Haynes et al. | 195/63 |
| 3,909,354 | 9/1975 | Thompson et al. | 195/31 |
| 4,111,750 | 9/1978 | Colilla et al. | 195/31 |
| 4,350,765 | 9/1982 | Chibata et al. | 435/161 |
| 4,506,012 | 3/1985 | Reed | 435/139 |
| 4,585,738 | 4/1986 | Roland | 435/176 |
| 4,670,387 | 6/1987 | Bucke et al. | 435/97 |
| 4,918,016 | 4/1990 | Leuba et al. | 435/176 |
| 4,925,803 | 5/1990 | Suehiro et al. | 435/288 |
| 5,079,011 | 1/1992 | Lommi et al. | 426/11 |
| 5,270,177 | 12/1993 | Lazcano et al. | 435/72 |
| 5,314,814 | 5/1994 | Harder et al. | 435/177 |
| 5,405,764 | 4/1995 | Harder et al. | 435/161 |
| 5,494,811 | 2/1996 | Scott et al. | 435/139 |
| 5,674,745 | 10/1997 | Humphrey et al. | 435/299.1 |

OTHER PUBLICATIONS

Oriol, Eric, et al.—Solid–State Culture of *Aspergillus niger* on Support *Journal of Fermentation Technology*, vol. 66, No. 1, pp. 57–62, 1988.

*Primary Examiner*—David M. Naff
*Attorney, Agent, or Firm*—Carla J. Dolce

[57] ABSTRACT

A biocatalyst for converting sucrose solutions to glucose-fructose solutions in a fluidized bed reactor is provided containing yeast adhered to a fibrous cellulose support. A method of making the biocatalyst is carried out by mixing yeast with water to form a yeast paste; mixing the yeast paste with a fibrous cellulose support to form a fiber-yeast mixture; treating the fiber-yeast mixture with a fixing agent; and drying the treated fiber-yeast mixture at a temperature not exceeding 70° C. The fibrous cellulose support preferably contains fibers ranging from approximately 0.5 cm to 3.0 cm in length obtained by processing of sugar cane bagasse or ground corn cobs. Preferably, the fixing agent is glutaraldehyde, cellulose triacetate, diethylaminoethyl-cellulose or a reaction product of polyethylenimine with 1,2-dichloroethane, and the yeast is *Saccharomyces cerevisiae*. A method for producing a glucose-fructose solution from a sucrose solution is provided containing the steps of passing the sucrose solution over the biocatalyst in a fluidized bed reactor and recovering the glucose-fructose solution.

14 Claims, 1 Drawing Sheet

FIBROUS CELLULOSE SUPPORT CONTAINING ADHERED YEAST FOR CONVERTING SUCROSE TO GLUCOSE AND FRUCTOSE

FIELD OF THE INVENTION

The invention relates to a biocatalyst for converting a sucrose solution to a glucose-fructose solution, and to a method for making the biocatalyst and for using it to produce glucose-fructose solutions from sucrose solutions.

BACKGROUND OF THE INVENTION

Sucrose may be converted to glucose-fructose either enzymatically with invertase or through acid hydrolysis. Industrial processes for producing glucose-fructose solutions from sucrose generally utilize an acid hydrolysis process which is expensive. Enzymatic processes generally require preparation of a biocatalyst comprised of the invertase enzyme or an invertase-producing microorganism immobilized on a support to prevent the enzyme or microorganism from being washed from the reactor. Presently known processes for producing such immobilized biocatalysts are not suitable for industrial use.

One process, described by Leuba, et al., in U.S. Pat. No. 4,918,016, discloses invertase immobilized on a chitosan-coated silica gel support and retaining significant enzymatic activity for converting sucrose to glucose-fructose. Leuba, et al. do not disclose use of their immobilized invertase in a continuous-flow reactor that might have industrial use. Another process described by Lazcano, et al., in U.S. Pat. No. 5,270,177, utilizes a recombinant yeast strain with the microorganism immobilized in calcium alginate. The process for producing the immobilized microorganism requires a specially-built needle device for dripping a sodium alginate solution containing the microorganism over a calcium chloride solution. Further, the alginate is relatively expensive for industrial use. Finally, the temperature range of the biocatalyst and method disclosed in Lazcano, et al. is limited to 40–50° C., further limiting industrial applications.

Numerous other methods for preparing and using immobilized microorganisms or enzymes have been described such as the methods and uses described by Colilla, et al., in U.S. Pat. No. 4,111,750; by Sipos in U.S. Pat. No. 3,708,397; by Lommi, et al., in U.S. Pat. No. 5,079,011, by Harder, et al., in U.S. Pat. No. 5,405,764, and by Harder, et al., in U.S. Pat. No. 5,314,814.

The methods known for immobilizing invertase or invertase-producing microorganisms for use as biocatalysts in the production of fructose are impractical for use on an industrial scale because such methods generally require expensive equipment or materials or involve complex processes. Moreover, in some existing methods, the support onto which the enzyme or microorganism is immobilized is easily compacted by the passage of solution over the support in a reactor. This compaction reduces the life of the biocatalyst.

Biocatalysts produced by presently known methods for immobilizing enzymes or microorganisms for production of fructose-glucose solutions are limited to operation at temperatures under 50° C. This limits the feed stocks that can be used to provide the sucrose solution. For example, molasses is too viscous at that temperature to be used as a feed stock. Finally, immobilized microorganisms or enzymes prepared by presently known methods remain enzymatically active for a relatively short time, generally less than a month, or must be stored in a sugar solution as in Lazcano, et al.

SUMMARY OF THE INVENTION

It is an object of the present invention to provide a biocatalyst, and a method for making the biocatalyst, for producing glucose-fructose solutions from sucrose solutions easily and inexpensively using readily-available fibrous cellulose support materials.

It is another object of the invention to provide a method for producing glucose-fructose solutions from sucrose solutions utilizing the biocatalyst of the invention in a fluidized bed reactor in a process that is substantially simpler than existing processes.

It is yet another object of the invention to provide a biocatalyst that resists compaction in a bioreactor having a continuous flow of sucrose substrate.

It is still another object of the invention to provide a biocatalyst for converting sucrose to fructose-glucose that may be stored for over a year at 25–30° C. without appreciable loss of enzymatic activity and that may be used in a bioreactor having a feed stock at a temperature of up to 70° C.

It is a further object of the present invention to provide a biocatalyst that remains enzymatically active in a bioreactor producing glucose-fructose from sucrose for over one year.

The foregoing objects and other objectives, features and advantages of the invention will be more readily understood from the following brief summary of the invention and the detailed description of the invention set forth below.

The invention relates to a biocatalyst for converting sucrose solutions to glucose-fructose solutions and to a simple method for making the biocatalyst. The biocatalyst is comprised of yeast adhered to a fibrous cellulose support. Adherence of the yeast to the fibrous cellulose material is facilitated by treatment with a fixing agent such as glutaraldehyde. The fibrous cellulose support with adhered yeast is dried and placed in a reactor or a series of reactors. Sucrose solution is passed through the reactors in series so the effluent of one reactor is the influent to the next reactor. Preferably, the reactors are fluidized bed reactors. The more reactors through which the sucrose solution is passed, the greater the percentage conversion to fructose and glucose. The effluent from the final reactor is recovered and evaporated to the desired concentration.

DETAILED DESCRIPTION OF THE INVENTION

Figure 1:
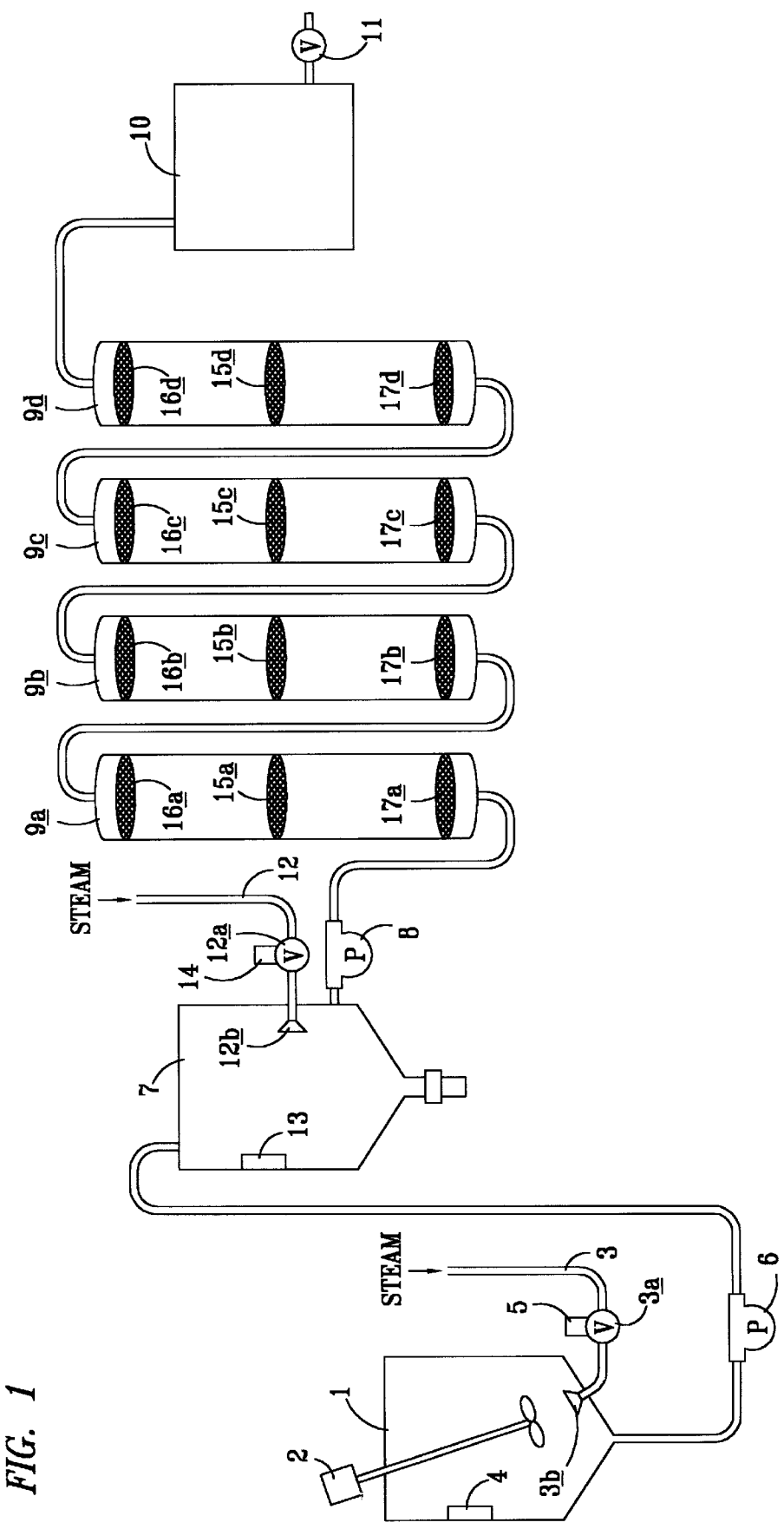
FIG. 1 depicts a flow process for production of a glucose-fructose solution from a sucrose solution in fluidized bed reactors.

The biocatalyst is comprised of yeast adhered to a fibrous cellulose support. Preferably, the yeast is baker's yeast or *Saccharomyces cerevisiae*. The fibrous cellulose support is preferably the processed sugar cane stalks that are a by-product from the milling of sugar cane, referred to herein as "sugar cane bagasse" or simply "bagasse." The fibrous cellulose support may also be ground corn cobs or other natural plant cellulose fiber material. Preferably, the fibrous cellulose support is comprised of fibers having a length of approximately 0.5 cm to 3.0 cm. Preferably, the biocatalyst has a moisture content of 3–4% water (by weight), but may be as high as 10%.

The biocatalyst is prepared by mixing yeast with water to form a paste. The yeast paste is further mixed with the fibrous cellulose support to form a fiber-yeast mixture. The fiber-yeast mixture is treated with a fixing reagent suitable for use in food products, such glutaraldehyde, cellulose triacetate, diethylaminoethyl-cellulose, and polyethyleiimine reaction product with 1,2-dichloroethane. The fiber-yeast mixture is then dried at a temperature not exceeding 70° C. to yield the biocatalyst.

The weight ratio of yeast to water to form the yeast paste is preferably 1:1, but may be up to 2:1. The fibrous cellulose support, which is preferably sugar cane bagasse of approximately 0.5 cm to 3.0 cm, is prepared by screening the fibrous cellulose support first through a screen mesh to remove fibers smaller than approximately 0.5 cm in length, then through a screen mesh to remove fibers longer than approximately 3.0 cm in length. The weight ratio of fibrous cellulose support to yeast is preferably approximately 1:1, but may vary from 2:1 to 1:2.

Fixing agent is added to the fiber-yeast mixture to facilitate adherence of the yeast to the fibrous cellulose support. Preferably, the fixing agent is glutaraldehyde. A 25% aqueous solution of glutaraldehyde may be added with the weight of the solution added being approximately one-half the weight of the fibrous cellulose support. The fiber-yeast mixture and glutaraldehyde solution are agitated for approximately 15 to 60 minutes.

After agitation, the fiber-yeast mixture, that has been treated with the fixing agent, is dried at a temperature of less than 70° C. to a moisture content of 3% to 4% water by weight. The moisture content may be as high as 10%. The resulting biocatalyst may be stored in a mesh bag for up to one year without appreciable loss of catalytic activity.

In the method for conversion of sucrose to glucose-fructose, the biocatalyst is placed in a reactor and a sucrose solution is passed through the reactor. The resulting glucose-fructose solution is recovered from the reactor. The sucrose solution may be in almost any form, for example, it may be raw or refined sugar dissolved in water; it may be molasses, or purified and concentrated fruit juice or any other source of sucrose at a concentration of approximately 55–65° Brix. Because the biocatalyst is more heat resistant than other biocatalysts known in the art, the substrate may be at a higher temperature than used with other known biocatalysts. The temperature of the substrate may be as high to 70° C. This permits the use of a greater variety of substrates, including molasses.

The conversion may take place in any reactor vessel in which the biocatalyst can be placed and sucrose solution passed through the bioreactor to effect the conversion. The following is provided by way of example for conversion of sucrose to glucose-fructose where the sucrose is either refined or raw sugar in solid form Generally, as depicted in FIG. 1, the sugar is dissolved in a dissolving tank (1), pumped by a pump (6) to a holding tank (7), pumped by a second pump (8) though a series of reactors (9a–9d) filled with the novel biocatalyst of the invention, and collected in a collecting tank (10).

More specifically, as depicted in FIG. 1, the sucrose is dissolved in the dissolving tank (1) with a mixer (2) to facilitate dissolution. The sugar is dissolved in sufficient water to create a sucrose syrup of approximately 55 to 65° Brix. The pH of the sucrose syrup should be between 4.5 and 5.5, and should be adjusted by conventional means if it is outside that range.

A means is provided to heat the sucrose preferably to a temperature of 55 to 65° C., but not more than 70° C. For example, as depicted in FIG. 1, the means for heating the sucrose solution may comprise a source of steam, a steam inlet conduit (3) connecting the dissolving tank (1) with the steam source, and a steam inlet valve (3a) connected to the steam inlet conduit (3) for selectively opening to permit steam to flow into the sucrose solution or closing to prevent the flow of steam into the sucrose solution. Preferably the steam inlet conduit (3) is connected to a steam diffusion head (3b) on the inside of the dissolving tank (1) so all the steam entering the sucrose solution is first diffused through the steam diffusion head (3b).

Preferably, the means for heating the sucrose solution further comprises a thermostat (4) and a steam inlet solenoid (5). The thermostat (4) is associated with the dissolving tank (1) for determining when the sucrose solution has reached a predetermined temperature. The steam inlet solenoid (5) is an electrically energized solenoid connected to the steam inlet valve (3a) and responsive to the thermostat (4) for opening the steam inlet valve (3a) when the thermostat (4) determines that the temperature of the sucrose syrup has fallen below a predetermined value, preferably 58° C. and for closing the steam inlet valve (3a) when the thermostat (4) determines that the sucrose solution has reached a second predetermined temperature, preferably 62° C.

A first pump (6) pumps the sucrose solution to a holding tank (7). To maintain the temperature of the sucrose, the holding tank may be insulated or heated as the dissolving tank is heated. If the sucrose in the holding tank is heated, a second steam inlet conduit (12), a second steam inlet valve (12a), a second diffuser (12b), and a second thermostat (13) are provided for keeping the sucrose syrup at a temperature of 55 to 65° C. Also provided is a second steam inlet solenoid (14), which is an electrically energized solenoid connected to the second steam inlet valve (12a) and responsive to the second thermostat (13) for opening the second steam inlet valve (12a) when the second thermostat (13) determines that the temperature of the sucrose syrup has fallen below a predetermined value, preferably 58° C. and for closing the second steam inlet valve (12a) when the second thermostat (13) determines that the sucrose solution has reached a predetermined temperature, preferably 62° C. As with the first steam inlet conduit, the second steam inlet conduit (12) is preferably connected to a second steam diffusion head (12b) on the inside of the holding tank (7) so all the steam entering the sucrose solution is first diffused through the steam diffusion head (12b).

A second pump (8) pumps the sucrose solution from the holding tank (7) through the reactors (9a–9d) which are placed in series. The reactors may be made of stainless steel or any other material approved for the production of food. The second pump (8) is preferably a peristaltic pump. Preferably, as shown in FIG. 1, the reactors are columnar fluidized bed reactors so that each reactor operates as a columnar chamber through which there is an upward flow of fluid that suspends or fluidizes the fibrous cellulose support fibers into an expanded bed. The sucrose syrup progresses through the suspended particles as essentially a front or "plug flow."

Depending upon the size of the reactors, each reactor may have one or more screen mesh supports (15a–15d), each having a mesh of approximately 0.3 cm. The screen mesh supports 15a–15d keep the fibrous cellulose support from compacting and may not be needed in smaller reactors. To keep the fibrous cellulose support from exiting the reactor with the fluid, a screen mesh (16a–16d) with a mesh of approximately 0.1 cm is provided in each reactor at the effluent end so all the sucrose exiting the reactor must pass through the screen. Likewise, to prevent the fibrous cellulose support from leaving the reactor with any back flow of sucrose through the inlet to the reactor, a screen mesh (17a–17d) with a mesh of approximately 0.1 cm is provided in each reactor at the influent end so all the sucrose entering the reactor must pass through the screen.

Preferably, water pressure meters (not shown in the drawings) are placed in the influent and effluent lines for the first reactor through which the sucrose passes to measure the drop in pressure as the fluid passes through the reactor for determining whether compaction has occurred.

As shown in FIG. 1, the process may include 4 reactors. Preferably, the process includes 2 banks of 4 reactors each so that sucrose flows independently through each bank of reactors into the same tank. Additional pumps are required. The process may include more reactors for each bank and more banks of reactors. The more reactors through which the sucrose is passed, the greater the percentage conversion to fructose and glucose. The resultant glucose-fructose solution is collected in the collecting tank (10) from the last reactor (9d).

The biocatalyst will remain enzymatically active in the reactor for more than one year even with continuous use. When the biocatalyst begins to lose its catalytic activity, it can be easily replaced.

Where the sucrose feed is molasses, the mixing tank (1) may be eliminated. The molasses must first be filtered to eliminate solid impurities. To decrease the viscosity of the molasses, the temperature in the holding tank (7) may be maintained at up to 70° C. Where other feed stocks are used, it may be necessary to adjust the temperature of the dissolving tank (1) and/or the holding tank (7).

Depending on the number of reactors used and the temperature of the air around the reactors, it may be necessary to insulate the reactors to minimize heat loss from the solution as it passes through the reactors. Alternatively, it may be necessary to add additional, thermostats, steam inlet conduits, and steam inlet solenoids between reactors to keep the temperature of the sucrose substrate at the desired level.

The entire process is readily automated with existing automation equipment.

EXAMPLE 1

Preparation of the Novel Biocatalyst

Sugar cane bagasse was screened first through a screen having a mesh of 0.5 cm. The fibers smaller than 0.5 cm were discarded and the larger fibers screened through a mesh of 3.0 cm. The fibers not passing through the 3.0 cm mesh, those longer than 3.0 cm, were discarded. The fibers between 0.5 and 3.0 cm were retained for use as the fibrous cellulose support to which the yeast will be adhered.

Yeast paste was made by mixing 12 kg of baker's yeast in 12 liters of water. The paste was mixed with a screw-type mixer. To the yeast paste was added 12 kg of fibrous cellulose support prepared as described above. The fibrous cellulose support was thoroughly mixed with the yeast paste forming a fiber-yeast mixture. To this fiber-yeast mixture, 6 liters of a 25% aqueous glutaraldehyde solution were added and mixed with the fiber-yeast mixture for 15 minutes.

At this point the yeast is adhered to the fibrous cellulose support. The resulting mixture was dried for one hour at approximately 60° C. to yield the biocatalyst with a moisture content of approximately 3–4%. The biocatalyst was stored in a mesh bag at 25–30° C. It can be stored for over one-year at this temperature without appreciable loss of catalytic activity.

EXAMPLE 2

Conversion of Sucrose to Glucose-fructose

For converting sucrose to glucose-fructose, two batteries of four columns each, with each column being 2.0 m high and 0.5 m in diameter may be filled with the biocatalyst prepared as described above. The columns should be interconnected so that the sucrose passes through them in series. Additionally, the columns should be operated as fluidized bed reactors. A solution of sucrose at 55 to 65° Brix, 55 to 65° C. and at a pH between 4.5 and 5.5 may be pumped through the columns filled with the biocatalyst using a peristaltic pump to obtain a flow rate of 3.458 gal/min. After 24 hours, approximately 95% of the sucrose will be inverted to glucose-fructose and 4,980 gal of glucose-fructose may be collected. This syrup may be concentrated by evaporation.

Although the present invention has been shown and described with respect to preferred embodiments, various changes and modifications which are obvious to a person skilled in the art to which the invention pertains are deemed to lie within the spirit and scope of the invention.

What I claim is:

1. A biocatalyst for converting sucrose solutions to glucose-fructose solutions in a fluidized bed reactor, the biocatalyst comprised of yeast adhered to a fibrous cellulose support with a fixing agent selected from the group consisting of glutaraldehyde, cellulose triacetate, diethylaminoethyl-cellulose, and polyethylenimine reaction product with 1,2-dichloroethane; the fibrous cellulose support comprised of fibers ranging from approximately 0.5 cm to 3.0 cm in length.

2. The biocatalyst of claim 1, further having a moisture content of 3% to 10% water by weight.

3. The biocatalyst of claim 1, wherein the yeast is *Saccharomyces cerevisiae*.

4. The biocatalyst of claim 1, wherein the fibrous cellulose support is selected from the group consisting of sugar cane bagasse and ground corn cobs, that has been processed to provide said fiber length.

5. A method of making a biocatalyst for converting sucrose solutions to glucose-fructose solutions in a fluidized bed reactor, comprising the steps of:
   a. mixing yeast with water to form a yeast paste;
   b. mixing the yeast paste with a fibrous cellulose support to form a fiber-yeast mixture, the fibrous cellulose support comprised of fibers ranging from approximately 0.5 cm to 3.0 cm in length;
   c. treating the fiber-yeast mixture with a fixing agent selected from the group consisting of glutaraldehyde, cellulose triacetate, diethylaminoethyl-cellulose, and polyethylenimine reaction product with 1,2-dichloroethane; and
   d. drying the treated fiber-yeast mixture at a temperature not exceeding 70°.

6. The method of claim 5, wherein the yeast is *Saccharomyces cerevisiae*.

7. The method of claim 5, wherein the fibrous cellulose support is selected from the group consisting of processed sugar cane bagasse and ground corn cobs, that has been processed to provide said fiber length 8. The method of claim 5 wherein the fixing agent is glutaraldehyde.

9. The method of claim 5, wherein the drying step further comprises drying the treated fiber-yeast mixture to a moisture content of between 3% and 10% water by weight.

10. A method for producing a glucose-fructose solution from a sucrose solution in a fluidized bed reactor comprising the steps of:

a. passing sucrose solution in a fluidized bed reaction over a biocatalyst comprised of yeast adhered to a fibrous cellulose support with a fixing agent selected from the group consisting of glutaraldehyde, cellulose triacetate, diethylaminoethyl-cellulose, and polyethylenimine reaction product with 1,2-dichloroethane, the fibrous cellulose support comprised of fibers ranging from approximately 0.5 cm to 3.0 cm in length, whereby invertase produced by the yeast converts the sucrose solution to a glucose-fructose solution; and, b. recovering the glucose-fructose solution.

11. The method of claim 10, wherein the biocatalyst has a moisture content of 3% to 10% water by weight.

12. The method of claim 10, wherein the yeast is *Saccharomyces cerevisiae*.

13. The method of claim 10, wherein the fibrous cellulose support is selected from the group consisting of processed sugar cane bagasse and ground corn cobs, that has been processed to provide said fiber length.

14. The method of claim 10, wherein the step of passing the sucrose solution over a biocatalyst comprises placing the biocatalyst in two or more columnar, fluidized bed reactors and passing the sucrose solution through the reactors in series.

* * * * *